United States Patent [19]

Miya et al.

[11] 4,144,198

[45] Mar. 13, 1979

[54] PROCESS FOR PREPARATION FOR COPPER-IRON-ALUMINUM CATALYSTS AND CATALYSTS PREPARED BY THE PROCESS

[75] Inventors: Bunji Miya; Yuzi Sawamoto; Kunizo Hashiba; Shizuo Hisamitsu, all of Wakayama, Japan

[73] Assignee: Kao Soap Co., Ltd., Tokyo, Japan

[21] Appl. No.: 863,131

[22] Filed: Dec. 22, 1977

[30] Foreign Application Priority Data

Jan. 25, 1977 [JP] Japan .................................. 52-7051

[51] Int. Cl.$^2$ ...................... B01J 21/04; B01J 23/72; B01J 23/74
[52] U.S. Cl. ................................ 252/466 J; 568/885
[58] Field of Search ................. 252/466 J; 260/638 A

[56] References Cited

U.S. PATENT DOCUMENTS

| | | | |
|---|---|---|---|
| 2,449,295 | 9/1948 | Gutzeit | 252/466 J |
| 2,844,633 | 7/1958 | Braconier et al. | 260/638 A |
| 3,197,418 | 7/1965 | Maebashi et al. | 260/638 A |

*Primary Examiner*—W. J. Shine
*Attorney, Agent, or Firm*—Blanchard, Flynn, Thiel, Boutell & Tanis

[57] ABSTRACT

Copper-iron-aluminum catalysts are prepared by dissolving a cupric salt, a ferrous salt and an aluminum salt in water, adding an alkali to the solution at a temperature higher than 60° C. whereby to form a precipitate, separating the precipitate and water-washing, drying, calcining and pulverizing the separated precipitate.

5 Claims, No Drawings

PROCESS FOR PREPARATION FOR COPPER-IRON-ALUMINUM CATALYSTS AND CATALYSTS PREPARED BY THE PROCESS

BACKGROUND OF THE INVENTION

1. FIELD OF THE INVENTION

The present invention relates to a process for preparing a copper-iron-aluminum catalyst for use in hydrogenation reactions.

2. DESCRIPTION OF THE PRIOR ART

Linear higher alcohols are prepared by reducing methyl esters of fatty acids with high pressure hydrogen at elevated temperatures. Copper-chromium oxide type catalysts, generally called "copper chromite catalysts," are used for this reaction. The original process for the production of catalysts of this type is described in Industrial and Engineering Chemistry, 26, page 878 (1936). No important improvements have previously been made in this basic process. The basic process comprises adding ammonia to a dichromate dissolved in water, adding a cupric salt thereto, filtering the resulting precipitate and then water-washing, drying and calcining the precipitate. In this process, the reaction is incomplete. Therefore, this process involves a serious disadvantage that copper ions and large quantities of hexavalent chromium ions are discharged in the waste water from the filtering and water-washing steps. In order to prevent environmental pollution, these heavy metals should be removed from the waste water by appropriate methods. However, a satisfactory way for finally disposing of the resulting heavy metal sludges has not been found.

In addition to the above disadvantage, the copper chromite catalyst involves another disadvantage which is that, because the particle size thereof is very small, the spent catalyst, after being used for the hydrogenation, cannot be effectively separated from the higher alcohol by filtration unless diatomaceous earth is added thereto as a filter aid. At present, the material that can be used as a filter aid is limited to diatomaceous earth. Because the copper chromite catalyst, after being once used for high pressure hydrogenation, still retains at least 90% of its original catalyst activity, it is desired that the catalyst be used again. However, if the recovered catalyst containing diatomaceous earth is used, the high pressure hydrogenation apparatus wears out rapidly. Thus, the catalyst is usually discarded after only one use. This is quite uneconomical. In addition, it is very expensive to take measures to insure that such spent catalyst does not cause environmental pollution.

SUMMARY OF THE INVENTION

We have discovered a copper-iron-aluminum catalyst which is a magnetic material and is an effective catalyst for hydrogenation reactions. The catalyst of the present invention is prepared by dissolving a cupric salt, a ferrous salt and an aluminum salt in water, adding an alkali to the solution at a temperature higher than 60° C. and up to 100° C. to form a precipitate, separating the precipitate, and water-washing, drying, calcining and pulverizing the separated precipitate. A part of the copper salt may be replaced by other salts, for example, a barium salt.

The process of the present invention has the following meritorious features:

(1) No heavy metals are discharged from the preparation process.

(2) Because the catalyst, after being used for the high pressure hydrogenation reaction, possesses a stronger magnetism than that of the catalyst before it is used, the spent catalyst can be separated from the higher alcohol by using a magnet. Because diatomaceous earth need not be used as a filter aid in the separation, the recovered catalyst can easily be used again. In addition, because the catalyst is free of chromium, disposal of the spent catalyst which has deteriorated because of repeated use can be accomplished much more easily than disposal of the known copper chromite catalyst. Still further, the catalyst activity can be completely restored in some cases by appropriate means, for example, recalcination of the spent catalyst.

As is apparent from the foregoing description, when the copper-iron-aluminum catalyst of the present invention is employed, the above-mentioned two serious disadvantages of the copper chromite catalyst can be eliminated. In addition to the foregoing features, the catalyst of the present invention has the following advantages:

(3) Whereas the copper chromite catalyst often causes accidents due to ignition, the catalyst of the present invention has no igniting property.

(4) The content of impurities in the alcohols prepared using the catalyst of the present invention is lower than that in the alcohols prepared using the copper chromite catalyst.

(5) The life of the catalyst of the present invention is longer than that of the copper chromite catalyst.

(6) The catalyst of the present invention does not deposit crystalline materials in the high-pressure hydrogenation column and thus does not clog the holes of the hydrogen sparger used therein.

(7) Since inexpensive iron salts and aluminum salts are used in place of an expensive dichromate, the manufacturing cost can be remarkably reduced.

The process for the preparation of the catalyst of the present invention will now be described in detail.

The water-soluble cupric salt that is used in the present invention includes various salts, such as cupric sulfate, cupric chloride and cupric nitrate. For economic reasons, cupric sulfate is most preferred. Ferrous sulfate, ferrous chloride and ferrous nitrate can be used as the water-soluble ferrous salt. Ferrous sulfate is most preferred. Aluminum sulfate, aluminum chloride, aluminum nitrate and various alums can be used as the water-soluble aluminum salt. Aluminum sulfate is most preferred. It is preferred that from 1.4 to 2.5 iron atoms and from 0.4 to 1.2 aluminum atoms be present per one atom of copper in the catalyst of the present invention. If the amount of the iron salt is below this range, the activity of the catalyst is high, but the magnetism of the catalyst after use is extremely weak. When the amount of the iron salt is too large, the magnetism is strong but the activity is low. In the preparation of a magnetic ferrite for electrical use, the molar ratio of the ferrous salt to the divalent metal salt is generally adjusted to be at least 2 and air is blown in during the reaction. However, in the case of the catalyst of the present invention, magnetism is manifested even if air is not blown into the reaction mixture if the atomic ratio of iron is higher than 1.4. As described previously, the catalyst obtains a stronger magnetism as a result of use as a hydrogenation catalyst.

When the atomic ratio of aluminum is lower than 0.4, the selectivity of the resulting catalyst is low, that is, a large amount of byproducts such as hydrocarbons and higher ethers are formed. If the atomic ratio of aluminum is higher than 1.2, the activity of the resulting catalyst is low.

As the alkali for forming the precipitate in the process of the present invention, there can be used lithium hydroxide, sodium hydroxide and potassium hydroxide. For cost reasons, sodium hydroxide is preferred. Lithium hydroxide is almost prohibitive in price. Potassium hydroxide is also expensive, but it provides a catalyst possessing excellent selectivity. Although potassium hydroxide is expensive, it can be used satisfactorily for industrial purposes, provided that the catalyst is recovered and used repeatedly.

When the stoichiometric amount of the alkali necessary for precipitating all of the copper, iron and aluminum in the aqueous solution, in the form of their hydroxides, is considered as being 100%, the amount of the alkali used in the present invention should be in the range of from 95 to 110%. Just after the alkali is added dropwise in such amount, the pH of the reaction mixture is in the range of from 9.5 to 11.8. At a lower or higher pH, the quality of the resulting catalyst is drastically degraded. Accordingly, the pH of the reaction mixture is more suitable as a reaction-monitoring key than the amount of the alkali. An optimum pH is in the range of from 10.8 to 11.5. In spite of such a high pH, the amount of the aluminum salt lost as sodium aluminate is very small. This fact means that in this reaction, the aluminum salt does not act independently. The alkali is conveniently diluted with water to, for example, a concentration of 30%. The addition of the alkali should be conducted gradually. The recipitate should be formed at a temperature higher than 60° C, but lower than the boiling point of the reaction mixture. If dropwise addition is conducted at a lower temperature, for example, at room temperature, the resulting catalyst has no substantial activity. The suspension containing a black precipitate formed by the addition of th alkali is agitated at the same temperature for from 10 minutes to 20 hours, preferably 1 to 7 hours.

In the X-ray diffraction pattern of the black precipitate formed by the above reaction, there are found no peaks of known simple oxides or hydroxides of Cu, Fe or Al, except $Cu_2O$. Since the black precipitate possesses magnetism, it is construed that it may contain a ferrite, but peaks characteristic of ferrites are not observed. The fact that the precipitate is black indicates that no metal hydroxide is present. The reason why no metal hydroxide is present is that both the pH and temperature of the reaction mixture are high. If the reaction is carried out at a low pH and temperature sufficient to allow the presence of metal hydroxides, for example, at a pH of 7 and room temperature, a substance having no catalytic activity is obtained.

After completion of the reaction, the precipitate is separated from the mother liquor by a convenient method such as filtration, magnetic separation or the like. In this separation, an anionic flocculant can be used effectively. The separated precipitate is washed with water several times to remove any residual soluble ions. A cationic flocculant is very effective for this water washing.

After water washing, the precipitate is dried by an appropriate method, and the dried product may be pulverized if necessary, but this pulverization can be omitted. The dried product is then calcined at a temperature of 450° to 850° C. An optimum calcination temperature is in the range of from 700° to 800° C. If the calcination temperature is lower than 450° C., a high activity is obtained but the catalyst life becomes extremely bad. If the calcination temperature is higher than 850° C., the activity is undesirably reduced and the catalyst particles are excessively sintered. The calcination is carried out for from 0 minute to 2 hours, calculated from the time at which the temperature of the dried product reaches the prescribed calcination temperature. The calcined product is pulverized to obtain the desired catalyst.

In the X-ray diffraction pattern of the resulting catalyst, peaks of $Fe_3O_4$ are observed, but no peaks of CuO, $Al_2O_3$, $Fe_2O_3$ and other simple substances are found. Further, peaks of a ferrite are not present. The magnetism of the catalyst which has been used for a high pressure hydrogenation is much stronger than that of the catalyst prior to such use, and the X-ray diffraction pattern of such used catalyst includes only peaks of $Fe_3O_4$.

EXAMPLE 1

In 1800 ml of water there were dissolved 0.24 mole of $CuSO_4 \cdot 5H_2O$, 0.36 mole of $FeSO_4 \cdot 7H_2O$ and 0.096 mole of $Al_2(SO_4)_3 \cdot 18H_2O$, and while maintaining the solution at 90° C., a 30% NaOH solution containing 1.776 moles of NaOH was added dropwise to the solution over a period of 30 minutes. At the end of the dropwise addition, the pH was 10.8. The mixture was agitated for 5 hours, and the precipitate was recovered by filtration. Cu ion was not detected in the filtrate and the Fe ion concentration was 0.5 ppm. The filtered precipitate was washed with water, dried, calcined at 750° C. for 1 hour, pulverized and passed through a 300-mesh sieve to obtain a catalyst.

To 150 g of methyl ester of coconut oil fatty acid was added 7.5 g of the above catalyst, and hydrogenation was carried out in a 500 cc autoclave under a hydrogen pressure of 150 Kg/cm$^2$ at a reaction temperature of 275° C. In order to remove methanol formed by the reaction, the gas was discharged at intervals of 30 minutes and fresh hydrogen was introduced. At times 30, 90, 150, 180, 210 and 240 minutes from the start of the reaction, small samples were taken and the saponification and hydroxyl values were determined after water washing. Assuming that the reaction is approximately first order, the rate constant k (hr$^{-1}$) was calculated from the saponification values of the starting material and that of the sample at 90 minutes. The samples after 180 minutes were analyzed for the sum of hydrocarbons and ethers. Since these impurities are formed according to the zero-order reaction, the rate constant B (%/hr) was calculated. (In Examples and Comparative Examples given hereinafter, all the analyses were the same unless otherwise indicated.) It was found that the rate constant k was 1.68 and the rate constant B was 1.71. In the same test with the conventional copper chromite catalyst, k was 1.61 and B was 3.65. Thus, it was confirmed that the catalyst of this Example is superior to the copper chromite catalyst with respect to the selectivity.

EXAMPLE 2

A test was made in the same manner as described in Example 1 except that the hydrogen pressure was adjusted to 250 Kg/cm$^2$ and discharge of the gas at intervals of 30 minutes was omitted. In the case of the catalyst of Example 1, k was 1.88 and B was 0.43, and in the case of the copper chromite catalyst, k was 2.00 and B was 0.85. Thus, it was confirmed that under the conditions of Example 2, the selectivity of the catalyst of the present invention also is higher than that of the copper chromite catalyst. In each of the two catalysts, the value B in Example 2 is smaller than the value B in Example 1, but the reason for this is unknown.

EXAMPLE 3

In 1800 ml of water there were dissolved 0.24 mole of $CuSO_4 \cdot 5H_2O$, 0.48 mole of $FeSO_4 \cdot 7H_2O$ and 0.072 mole of $Al_2(SO_4)_3 \cdot 18H_2O$, the solution was maintained at 90° C., and a 30% NaOH solution containing 1.916 moles of NaOH was added dropwise to the solution over a period of 30 minutes. At the end of the dropwise addition, the pH was 11.5. The mixture was agitated for 5 hours, and the precipitate was recovered by filtration and washed with water. Sodium polyacrylate was used as an anionic flocculant during the filtration and an acrylamide-dimethylaminoethyl methacrylate copolymer was used as a cationic flocculant during the water washing. Then, the water-washed precipitate was treated in the same manner as described in Example 1 to obtain a catalyst.

To 150 g of methyl ester of coconut oil fatty acid was added 7.5 g of the above catalyst, and the reaction was carried out under a hydrogen pressure of 250 Kg/cm² at a reaction temperature of 275° C. for 3 hours. The catalyst was separated from the reaction product, and the saponification value of the product was determined. The separated catalyst was used for the second reaction as it was. These procedures were repeated several times. The conventional copper chromite catalyst was similarly tested. The results obtained were as follows.

without ignition. In the same test on the copper chromite catalyst, the catalyst ignited at 110° C. When these used catalysts were examined under an electron microscope, deposition of crystals was not observed in the catalyst of Example 1 but deposition of many copper crystals having a size of about 10 μ was observed in the copper chromite catalyst.

EXAMPLE 7

To 200 g of furfural were added 0.8 g of $Ca(OH)_2$ and 1.6 g of the catalyst of Example 1, and the furfuryl alcohol was prepared under a hydrogen pressure of 120 Kg/cm² and at a temperature of 160° C. The reaction was completed in 15 minutes. The product was found to comprise 97.6% of furfuryl alcohol and 0.2% of unreacted furfural.

Japanese Patent Publication No. 7287/70 discloses a process for reducing a fatty acid ester to a higher alcohol in the presence of an Fe—Cu—O catalyst. The characteristic feature of the disclosed invention is that a catalyst, prepared by adding an alkali to a mixed aqueous solution of a copper salt and an iron salt to precipitate hydroxides, and by water-washing, dehydrating, drying, calcining and pulverizing the precipitate, is used at a temperature of 200° to 260° C. for reduction of esters and the like. It is taught that if a small amount of aluminum, chromium or zinc is incorporated in this catalyst, the formation of hydrocarbons can be controlled to some extent. In all the Examples, the pH is 7 at the end of addition of the alkali, and the calcination temperature is 400° C. This Patent Publication does not specifically describe the temperature of addition of the alkali. This fact suggests that the dropwise addition is

| Number of Cycles of Reaction | Saponification Values | | | | | | | | | |
|---|---|---|---|---|---|---|---|---|---|---|
| | 1 | 2 | 3 | 4 | 5 | 6 | 7 | 8 | 9 | 10 |
| Catalyst of This Example | 6.5 | 6.5 | 7.0 | 12.8 | 18.3 | 27.8 | 37.0 | 49.0 | 55.2 | 75.0 |
| Copper Chromite Catalyst | 6.6 | 6.3 | 7.2 | 11.4 | 19.5 | 30.8 | 59.7 | 75.4 | 88.0 | 106.2 |

From the above results, it is readily understood that the catalyst life of this Example is superior to that of the copper chromite catalyst.

EXAMPLE 4

A catalyst was prepared in the same manner as described in Example 1 except that KOH was used instead of NaOH. The hydrogenation was carried out with this catalyst in the same manner as described in Example 1. The value of rate constant B was 1.55.

EXAMPLE 5

A catalyst was prepared in the same manner as described in Example 1 except that each of $CuSO_4 \cdot 5H_2O$, $FeSO_4 \cdot 7H_2O$, $Al_2(SO_4)_3 \cdot 18H_2O$ and NaOH was used in an amount 5 times the amount used in Example 1. The properties of the resulting catalyst were substantially the same as those of the catalyst prepared in Example 1. However, in this Example, the filtration and water-washing of the precipitate were slightly more difficult than in Example 1.

EXAMPLE 6

The catalyst prepared in Example 1 was used for the reaction. The used catalyst was readily attracted by a magnet. The used catalyst which was washed with methanol to remove oil could be heated up to 180° C.

probably conducted at room temperature. In fact, since it is disclosed that the metals are coprecipitated in the form of hydroxides and the calcined catalyst consists of $Fe_2O_3$ and CuO, it is apparent that the dropwise addition is carried out at room temperature. At such low temperature, the copper salt and iron salt are coprecipitated but they act independently. Accordingly, the resulting catalyst comprises both $Fe_2O_3$ and CuO. As is described hereinafter, the precipitate formed at such low temperature is not black, but rather is brown.

In contrast, according to the process of the present invention, as described hereinbefore, the temperature and pH are much higher during the alkali addition step and the precipitate is a black substance having magnetism. In the X-ray diffraction pattern of a catalyst obtained by calcining this black precipitate, peaks of CuO and $Fe_2O_3$ are not observed. Accordingly, it is apparent that the catalyst of the present invention is a copper-iron-aluminum composite having a composition quite different from that of the catalyst disclosed in Japanese Patent Publication No. 7287/70.

As described above, the temperature and pH adopted for the formation of a precipitate in the invention of Japanese Patent Publication No. 7287/70 are very low. For this reason, the catalytic activity of the resulting catalyst is questionable. Accordingly, in the following Comparative Example, catalysts were prepared according to the teaching given in Examples of this Patent Publication, and their properties were tested.

COMPARATIVE EXAMPLE

According to the teachings given in Example 4 of Japanese Patent Publication No. 7287/70, 0.6 mole of $Fe(NO_3)_3 \cdot 9H_2O$, 0.12 mole of $Cu(NO_3)_2 \cdot 3H_2O$ and 0.03 mole of $Al(NO_3)_3 \cdot 9H_2O$ were dissolved in 2 l of water and aqueous ammonia was added to adjust the pH to 7 and to coprecipitate metal hydroxides. By this coprecipitation, a brown precipitate was obtained. The precipitate was washed with water, dehydrated, dried and calcined at 400° C. for 1 hour to obtain a catalyst. With this catalyst, a hydrogenation was carried out under the same conditions as described in Example 1 except that the reaction temperature was adjusted to 220° C. However, the catalyst did not show any activity at all. When the reaction temperature was elevated to 275° C., the value of rate constant k was only 0.22, and the total amount of hydrocarbons and ethers was 8.5% at 30 minutes from the start of the reaction, 15.1% at 90 minutes, 22.7% at 150 minutes and 26.2% at 180 minutes. Thus, it was found that the selectivity was extremely bad.

According to the teachings given in Example 16 of the above Patent Publication, a mixed aqueous solution containing $CuSO_4$ and $FeSO_4$ at a molar ratio of 20/100 was prepared and NaOH was added thereto to coprecipitate hydroxides. The precipitate was washed sufficiently with water, dehydrated, dried, calcined at 400° C for 1 hour and pulverized. With this catalyst, the hydrogenation was carried out under the same conditions as described in Example 1 except that the reaction temperature was adjusted to 240° C. The value of rate constant k was only 0.05, and the acid value of the sample at 180 minutes from the start of the reaction was 25.6 (the acid value of the product prepared with the catalyst of the present invention is lower than 0.1). Accordingly, it is apparent that such catalyst is unsuitable for industrial use. When the reaction temperature was elevated to 275° C., because of decomposition, the hydroxyl value of the sample at 180 minutes was 0.0.

$Cr_2O_3$ and ZnO were respectively incorporated in the above mixed aqueous solution in an amount of 50 and 200 molar ratio, according to Example 22 and 23 of the above Patent Publication, and a catalyst was similarly prepared and tested, but it was found that such catalyst is not industrially useful.

It is apparent that the catalyst disclosed in the above Japanese Patent Publication is quite different from the catalyst of the present invention with respect to its composition and activity, even though the two catalysts can be prepared from the same starting materials.

The embodiments of the invention in which an exclusive property or privilege is claimed are defined as follows:

1. A process for preparing copper-iron-aluminum catalysts, which comprises dissolving a cupric salt, a ferrous salt and an aluminum salt in water in proportions such that the solution contains 1.4 to 2.5 iron atoms and 0.4 to 1.2 aluminum atoms per one atom of copper, adding an alkali to the solution at a temperature higher than 60° C. and lower than the boiling point of the solution until the pH of the solution is in the range of from 9.5 to 11.8 to form a precipitate, separating the precipitate and then water-washing, drying, calcining and pulverizing the separated precipitate.

2. A process for the preparation of copper-iron-aluminum catalysts according to claim 1 wherein the copper salt is cupric sulfate, the iron salt is ferrous sulfate and the aluminum salt is aluminum sulfate.

3. A process according to claim 1, which consists essentially of dissolving in water (a) a cupric salt selected from the group consisting of cupric sulfate, cupric chloride and cupric nitrate, (b) a ferrous salt selected from the group consisting of ferrous sulfate, ferrous chloride and ferrous nitrate, and (c) an aluminum salt selected from the group consisting of aluminum sulfate, aluminum chloride and aluminum nitrate, to form an aqueous reaction mixture containing from 1.4 to 2.5 atoms of iron and 0.4 to 1.2 atoms of aluminum, per one atom of copper, gradually adding an aqueous solution of an alkali metal hydroxide to said reaction mixture and mixing same therein, at a temperature of from 60° C. to the boiling temperature of the reaction mixture, to change the pH of said reaction mixture to from 9.5 to 11.8, then maintaining said reaction mixture at said temperature for from 10 minutes to 20 hours while agitating said reaction mixture containing a black precipitate suspended therein, then separating said precipitate from the remainder of the reaction mixture, washing the precipitate with water to remove water-soluble ions, then drying the precipitate calcining the dried product at 450° to 850° C. for a period of time at the calcination temperature of from 0 to 2 hours to obtain a catalyst product.

4. A catalyst prepared by the process of claim 1.

5. A catalyst prepared by the process of claim 3.

* * * * *